US00PP31026P2

(12) United States Plant Patent
Klemm et al.

(10) Patent No.: US PP31,026 P2
(45) Date of Patent: Nov. 5, 2019

(54) ***OSTEOSPERMUM* PLANT NAMED 'KLEOE19396'**

(50) Latin Name: ***Osteospermum ecklonis* Norl.**
Varietal Denomination: KLEOE19396

(71) Applicant: Klemm+Sohn GmbH & Co. KG, Stuttgart (DE)

(72) Inventors: Nils Klemm, Stuttgart (DE); Maike Boxriker, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/350,301

(22) Filed: Oct. 29, 2018

(51) Int. Cl.
*A01H 5/02* (2018.01)
*A01H 6/14* (2018.01)

(52) U.S. Cl.
USPC ..... Plt./360

(58) Field of Classification Search
USPC ..... Plt./360
See application file for complete search history.

*Primary Examiner* — Susan McCormick Ewoldt
(74) *Attorney, Agent, or Firm* — Bethany R. Roahrig; Cochran Freund & Young LLC

(57) ABSTRACT

A new *Osteospermum* plant particularly distinguished by tri-colored flowers and an upright growth habit, is disclosed.

1 Drawing Sheet

Genus and species: *Osteospermum ecklonis* Norl.
Variety denomination: 'KLEOE19396'.

BACKGROUND OF THE NEW PLANT

The present invention comprises a new and distinct variety of *Osteospermum*, botanically known as *Osteospermum ecklonis* Norl., and hereinafter referred to by the variety name 'KLEOE19396'. 'KLEOE19396' originated from a cross-pollination conducted in August to September 2015 in Stuttgart, Germany between the proprietary female *Osteospermum* variety 'OE-2013-0045' (unpatented), and the male *Osteospermum* variety 'Blue Eyed Beauty', also known as 'Balostlueye' (U.S. Plant Pat. No. 26,150).

The seeds from the cross were sown and plants were grown in a greenhouse for evaluation, where an individual plant designated 'KLEOE19396' was selected from the group of plants in April 2016 in Stuttgart, Germany. In September 2016 in Stuttgart, Germany, 'KLEOE19396' was first vegetatively propagated by vegetative terminal cuttings. 'KLEOE19396' was found to reproduce true to type in successive generations of asexual propagation via vegetative terminal cuttings.

SUMMARY

The following are the most outstanding and distinguishing characteristics of this new variety when grown under normal horticultural practices in Stuttgart, Germany.

1. Tri-colored flowers; and
2. An upright growth habit.

DESCRIPTION OF THE PHOTOGRAPH

This new *Osteospermum* plant is illustrated by the accompanying photograph which shows the plant's overall plant habit including form, foliage, and flowers. The photograph is of an 11-week-old plant grown in a greenhouse in Stuttgart, Germany in August 2018. The colors shown are as true as can be reasonably obtained by conventional photographic procedures.

DESCRIPTION OF THE NEW VARIETY

The following detailed descriptions set forth the distinctive characteristics of 'KLEOE19396'. The data which define these characteristics were collected in Stuttgart, Germany in October 2018 on plants that had been planted in February 2018. Color references are to The R.H.S. Colour Chart of The Royal Horticultural Society of London (R.H.S.), 5$^{th}$ edition (2007).

Classification:
- *Family.*—Asteraceae.
- *Botanical.*—*Osteospermum ecklonis.*
- *Common.*—*Osteospermum.*
- *Designation.*—'KLEOE19396'.

Parentage:
- *Female parent.*—The proprietary female *Osteospermum* variety 'OE-2013-0045' (unpatented).
- *Male parent.*—The male *Osteospermum* variety 'Blue Eyed Beauty' (U.S. Plant Pat. No. 26,150).

Plant:
- *Form and habit.*—Herbaceous perennial but usually cultivated as an annual; not frost resistant.
- *Growth habit.*—Upright.
- *Branching habit.*—Normal.
- *Height (from top of soil, including inflorescence).*—35.0 cm.
- *Width (including inflorescences).*—50.0 cm.
- *Propagation type.*—Stem cuttings; vegetative terminal tip cuttings.
- *Time to produce a finished flowering plant.*—9 weeks.
- *Time to initiate and develop roots.*—4 weeks.
- *Root description.*—Fine and white.

Stems:
- *Total number of branches per plant (calculated at the base of the plant).*—3.
- *Length.*—28.0 cm.

*Diameter.*—0.5 cm.
*Internode length.*—1.7 cm.
*Color.*—RHS 144B.
*Texture.*—Smooth, but with fine hairs.
*Anthocyanin.*—RHS 184C.

Leaves:
*Arrangement.*—Alternate.
*Shape.*—Obovate.
*Apex.*—Acute.
*Base.*—Acute.
*Margin.*—Entire.
*Immature color.*—Upper surface: RHS 137B. Lower surface: RHS 138A.
*Mature color.*—Upper surface: RHS 137A. Lower surface: RHS 137C. Length: 4.7 cm. Width: 1.7 cm.
*Texture.*—Upper surface: Leathery. Lower surface: Leathery with fine hairs.
*Petioles.*—Absent.
*Venation pattern.*—Pinnate.
*Venation color (both surfaces).*—RHS 137A.

Flower buds:
*Shape.*—Round-ovoid.
*Length.*—1.0 cm.
*Diameter.*—1.3 cm.
*Color (at tight bud just before the ray florets unfold).*—RHS 137B.

Inflorescence:
*Type.*—Composite, single.
*Blooming habit.*—Upright, with longer flower stems.
*Quantity of inflorescences per plant.*—8.
*Lastingness of the inflorescences on the plant.*—10 to 15 days.
*Fragrance.*—Present, sweet.
*Inflorescence diameter.*—6.0 cm.
*Inflorescence depth.*—0.7 cm.
*Disc diameter.*—1.2 cm.

Disc floret:
*Quantity per inflorescence.*—About 30.
*Shape.*—Tubular.
*Tube color.*—Closed: RHS NN155A. Mature: RHS N155B.
*Length.*—1.7 cm.
*Diameter (at apex).*—0.1 cm.
*Apex.*—Acute.
*Apex color.*—RHS 79A.
*Base.*—Acute.
*Base color.*—RHS 145D.
*Margin.*—Entire.

Ray floret:
*Quantity per inflorescence.*—24.
*Shape.*—Oblanceolate.
*Color.*—Upper surface: RHS 14A (apical), RHS 28A (Middle), and RHS N79C (basal). Lower surface: Main color RHS 15A with stripes colored RHS N79A.
*Length.*—2.5 cm.
*Width.*—0.7 cm.
*Apex.*—Acute.
*Base.*—Acute.
*Margin.*—Entire.
*Texture.*—Upper surface: Smooth. Lower surface: Smooth, shiny.

Peduncle:
*Length.*—2.0 cm.
*Diameter.*—0.2 cm.
*Texture.*—Smooth with hairs.
*Color.*—RHS 143C.

Phyllaries:
*Arrangement.*—Single.
*Observed quantity per flower.*—19.
*Shape.*—Lanceolate.
*Apex.*—Acute.
*Base.*—Obtuse.
*Margin.*—Entire.
*Length.*—1.1 cm.
*Width.*—0.2 cm.
*Texture.*—Upper surface: Smooth with fine hairs. Lower surface: Smooth.
*Color (both surfaces).*—RHS 143B.

Reproductive organs:
*Androecium.*—Location: On disc and ray florets. Stamens: Shape: Filamentous. Quantity: Numerous, 30 to 50. Filament length: 0.8 cm. Filament diameter: 0.1 cm. Anther: Shape: Lanceolate. Color: RHS N77A. Length: 0.1 cm. Diameter: Greater than 0.1 cm. Pollen: Color: RHS 17A. Amount: Sparse.
*Gynoecium.*—Location: On the phyllary. Pistils: Number: Numerous, 30 to 50. Length: 0.8 cm. Diameter: 0.2 cm. Stigma: Color: RHS 79A. Shape: Tapering filamentous and split in two parts. Length: 0.1 cm. Diameter: Greater than 0.1 cm. Style: Color: RHS 155A. Length: 0.4 cm. Diameter: Greater than 0.1 cm.

Seed:
*Color.*—RHS 200D.
*Shape.*—Ovate.
*Length.*—0.5 cm.
*Width.*—0.2 cm.

Disease and pest/insect resistance: No disease and pest/insect resistance observed.

COMPARISON WITH PARENTAL LINES AND KNOWN VARIETY

'KLEOE19396' is a distinct variety of *Osteospermum* and is distinguished from its parents as described in Table 1.

TABLE 1

Comparison with Parental Lines

| Characteristic | 'KLEOE19396' | Female Parent 'OE-2013-0045' | Male Parent 'Blue Eyed Beauty' |
|---|---|---|---|
| Flower Color | Tri-colored | Bi-colored | Bi-colored |
| Branching | Good | Good | Medium |

'KLEOE19396' is most similar to the commercial *Osteospermum* variety 'KLEO13209'. Differences between the varieties are described in Table 2.

TABLE 2

Comparison with Similar Variety

| Characteristic | 'KLEOE19396' | 'KLEO13209' |
|---|---|---|
| Flower color | Tri-colored | Bi-colored |
| Branching | Good | Less than 'KLEOE19396' |
| Summer performance | Till autumn | Less flowers than 'KLEOE19396' at autumn |

We claim:

1. A new and distinct variety of *Osteospermum* plant designated 'KLEOE19396' as illustrated and described herein.

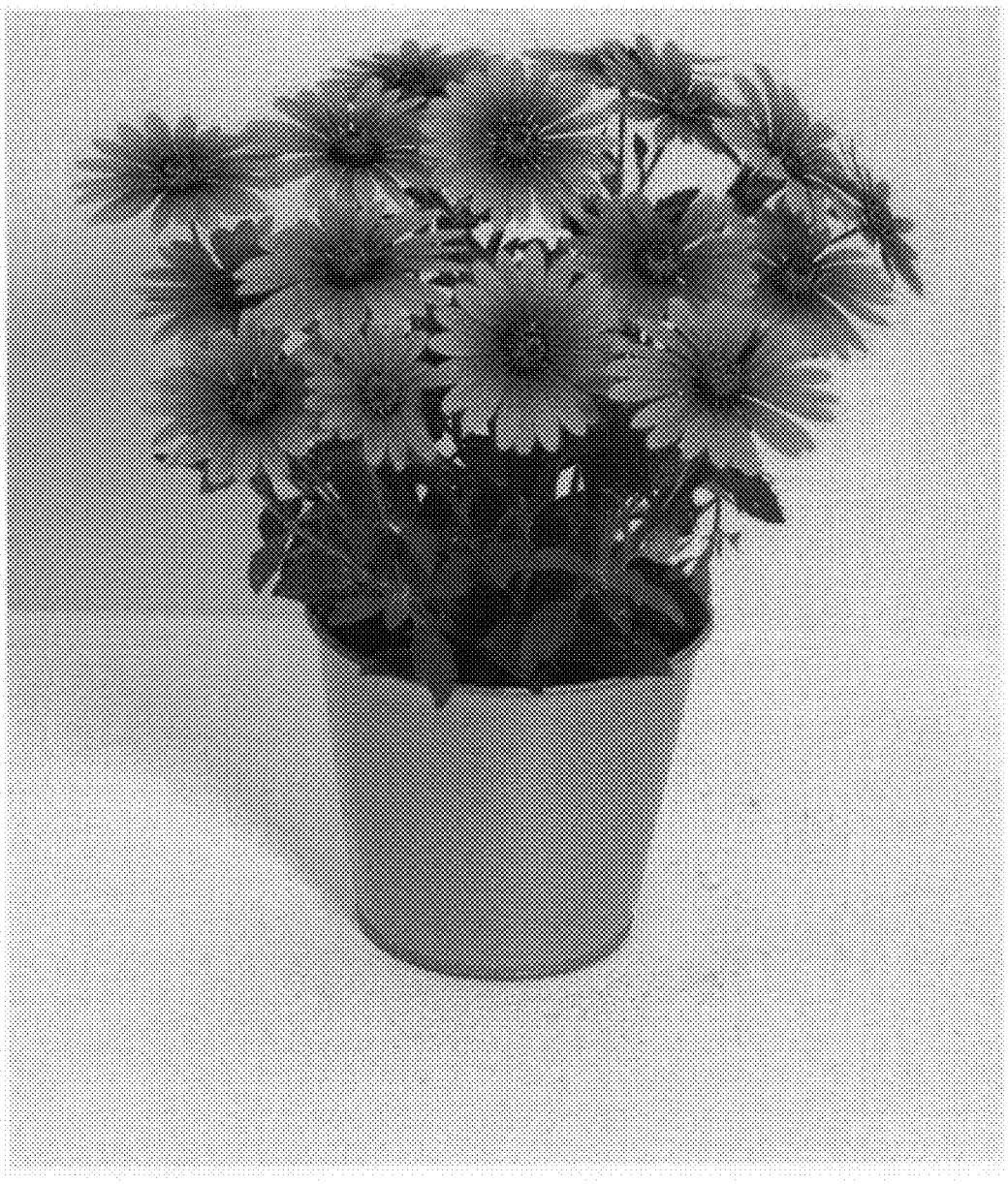

* * * * *